United States Patent
Ebling et al.

(10) Patent No.: US 8,775,573 B2
(45) Date of Patent: Jul. 8, 2014

(54) METHOD AND APPARATUS FOR LOCALIZED ADAPTATION OF CLIENT DEVICES BASED ON CORRELATION OR LEARNING AT REMOTE SERVER

(75) Inventors: Maria Rene Ebling, White Plains, NY (US); William Francis Jerome, Baldwin Place, NY (US); Archan Misra, Ardsley, NY (US); Iqbal I. Mohomed, Toronto, CA (US)

(73) Assignee: International Business Machines Corporarion, Armonk, NY (US)

( * ) Notice: Subject to any disclaimer, the term of this patent is extended or adjusted under 35 U.S.C. 154(b) by 339 days.

(21) Appl. No.: 12/125,464

(22) Filed: May 22, 2008

(65) Prior Publication Data

US 2008/0222246 A1 Sep. 11, 2008

Related U.S. Application Data

(63) Continuation of application No. 11/453,593, filed on Jun. 15, 2006, now abandoned.

(51) Int. Cl.
| | |
|---|---|
| G06F 15/177 | (2006.01) |
| G06F 15/16 | (2006.01) |
| A61B 5/00 | (2006.01) |
| H04L 29/08 | (2006.01) |
| A61B 5/1495 | (2006.01) |

(52) U.S. Cl.
CPC ............. *H04L 67/12* (2013.01); *A61B 5/1495* (2013.01)
USPC ........... 709/220; 709/217; 709/219; 709/221; 709/222; 600/300

(58) Field of Classification Search
CPC .. H04L 67/12; A61B 5/1495; A61B 5/14552; G06K 19/06037
USPC .......................... 709/203, 217–225; 600/300; 455/417–420
See application file for complete search history.

(56) References Cited

U.S. PATENT DOCUMENTS

| | | | |
|---|---|---|---|
| 6,221,011 B1 * | 4/2001 | Bardy | ............................ 600/300 |
| 6,454,708 B1 | 9/2002 | Ferguson et al. | |

(Continued)

FOREIGN PATENT DOCUMENTS

| | | |
|---|---|---|
| EP | 1533373 A1 | 5/2005 |
| JP | 2002304201 A | 10/2002 |

(Continued)

OTHER PUBLICATIONS

C. Olston et al., "Offering a Precision-Performance Tradeoff for Aggregation Queries Over Replicated Data," Proceedings of the 26th VLDB Conference, pp. 144-155, 2000.

(Continued)

*Primary Examiner* — Catherine Thiaw
(74) *Attorney, Agent, or Firm* — Anne V. Dougherty; Ryan, Mason & Lewis, LLP

(57) ABSTRACT

Techniques are disclosed for localized adaptation of client devices based on correlation or learning at a remote server. For example, a method for modifying a behavior of a client device in a data collection system, wherein the client device collects data and transmits data to a server, includes the following steps. The client device transmits data to the server. The server uses at least a portion of the data received from the client device to generate information that represents a modification to a behavior of the client device. The server device transmits the generated information to the client device. The client device subsequently alters the behavior of the client device based on the information received from the server.

34 Claims, 5 Drawing Sheets

(56) References Cited

U.S. PATENT DOCUMENTS

| | | | |
|---|---|---|---|
| 6,519,627 B1* | 2/2003 | Dan et al. | 709/203 |
| 6,553,336 B1 | 4/2003 | Johnson et al. | |
| 6,607,485 B2* | 8/2003 | Bardy | 600/300 |
| 7,155,507 B2* | 12/2006 | Hirano et al. | 709/224 |
| 7,276,029 B2 | 10/2007 | Goode et al. | 600/365 |
| 7,415,308 B2* | 8/2008 | Gerber et al. | 607/41 |
| 7,654,956 B2* | 2/2010 | Brister et al. | 600/365 |
| 7,834,754 B2* | 11/2010 | Kulesz et al. | 340/506 |
| 2003/0014217 A1* | 1/2003 | Warner et al. | 702/182 |
| 2003/0100821 A1* | 5/2003 | Heller et al. | 600/347 |
| 2003/0195399 A1 | 10/2003 | Phipps | |
| 2003/0212311 A1 | 11/2003 | Nova et al. | |
| 2004/0015058 A1* | 1/2004 | Besson et al. | 600/301 |
| 2004/0181604 A1 | 9/2004 | Immonen | |
| 2004/0199409 A1 | 10/2004 | Brown | |
| 2004/0254652 A1 | 12/2004 | Ota et al. | |
| 2005/0131736 A1* | 6/2005 | Nelson et al. | 705/2 |
| 2005/0198228 A1* | 9/2005 | Bajwa et al. | 709/220 |
| 2005/0206518 A1* | 9/2005 | Welch et al. | 340/539.12 |
| 2005/0222895 A1 | 10/2005 | Jakobson et al. | |
| 2006/0004923 A1* | 1/2006 | Cohen et al. | 709/228 |
| 2006/0052882 A1 | 3/2006 | Kubach et al. | |
| 2006/0064477 A1 | 3/2006 | Renkis | |
| 2006/0149905 A1* | 7/2006 | Park et al. | 711/141 |
| 2006/0155818 A1* | 7/2006 | Odenwald et al. | 709/208 |
| 2006/0206011 A1* | 9/2006 | Higgins et al. | 600/300 |
| 2006/0246436 A1 | 11/2006 | Ohno et al. | |
| 2006/0271661 A1* | 11/2006 | Qi et al. | 709/223 |
| 2006/0293571 A1* | 12/2006 | Bao et al. | 600/300 |
| 2007/0156450 A1* | 7/2007 | Roehm et al. | 705/2 |
| 2007/0156626 A1* | 7/2007 | Roehm et al. | 706/924 |
| 2007/0168310 A1* | 7/2007 | Kaminsky et al. | 706/47 |
| 2007/0182544 A1* | 8/2007 | Benson et al. | 340/521 |
| 2007/0192763 A1* | 8/2007 | Helvick | 717/168 |
| 2007/0260470 A1* | 11/2007 | Bornhoevd et al. | 705/1 |
| 2007/0266078 A1* | 11/2007 | Rittle et al. | 709/203 |
| 2008/0214903 A1* | 9/2008 | Orbach | 600/301 |
| 2008/0307076 A1* | 12/2008 | Ewing et al. | 709/220 |
| 2009/0037220 A1* | 2/2009 | Chambers et al. | 705/3 |
| 2009/0132540 A1* | 5/2009 | Hjelm et al. | 707/10 |

FOREIGN PATENT DOCUMENTS

| | | |
|---|---|---|
| JP | 2003115092 A | 4/2003 |
| JP | 2003141662 A | 5/2003 |
| JP | 2004000018 A | 1/2004 |
| JP | 2004174168 A | 6/2004 |
| JP | 2005115799 A | 4/2005 |
| JP | 2005122655 A | 5/2005 |
| TW | 462000 B | 11/2001 |
| TW | 473684 B | 1/2002 |
| WO | 03/097830 A1 | 11/2003 |
| WO | 2006011124 A1 | 2/2006 |
| WO | PCTEP2007055942 | 3/2008 |

OTHER PUBLICATIONS

C. Olston et Al., "Adaptive Precision Setting for Cached Approximate Values," Proceedings of the 2001 ACM SIGMOD International Conference on Management of Data, ACM Press, pp. 355-366, 2001.

Q. Han et Al., "Energy Efficient Data Collection in Distributed Sensor Environments," Proceedings of the 24th International Conference on Distributed Computing Systems, IEEE Computer Society, pp. 590-597, 2004.

A.K. Dey et Al., "A Conceptual Framework and a Toolkit for Supporting the Rapid Prototyping of Context-aware Applications," Human-Computer Interaction (HCI) Journal, vol. 16, pp. 1-67, 2001.

M.C. Huebscher et al., "Adaptive Middleware for Context-aware Applications in Smart-Homes," Proceedings of the 2nd International Workshop on Middleware for Pervasive and Ad-Hoc Computing (MPAC), vol. 77, 6 pages, 2004.

U.S. Appl. No. 11/365,215, filed Mar. 1, 2006, A. Misra et al.

W.B. Heinzelman et al., "Middleware to Support Sensor Network Applications," IEEE Network, Jan./Feb. 2004, pp. 6-14.

* cited by examiner

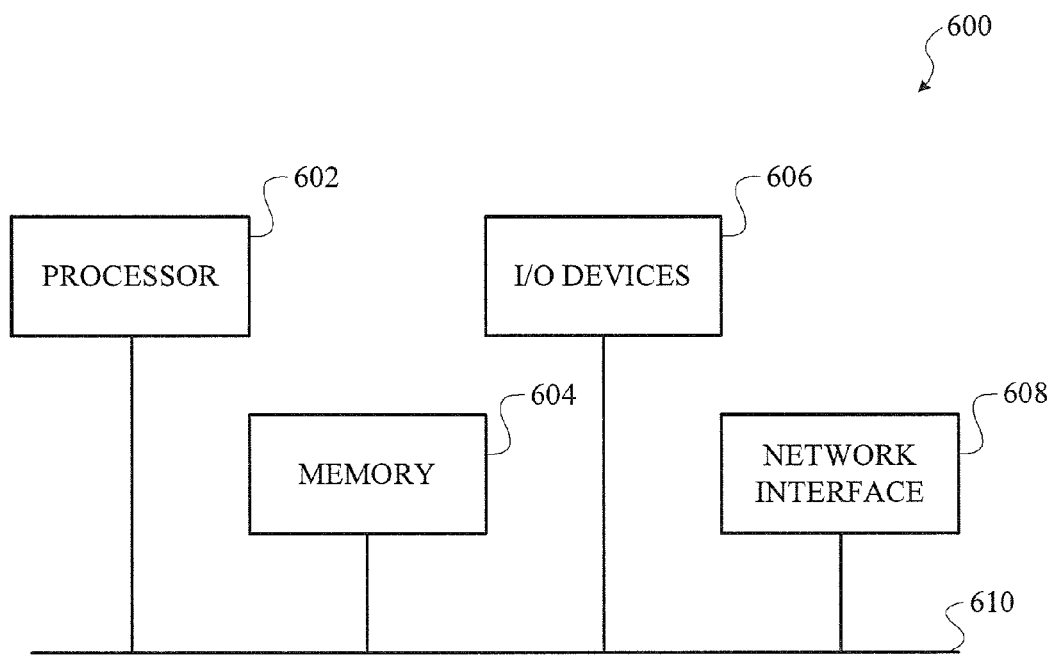

METHOD AND APPARATUS FOR LOCALIZED ADAPTATION OF CLIENT DEVICES BASED ON CORRELATION OR LEARNING AT REMOTE SERVER

CROSS-REFERENCE TO RELATED APPLICATION(S)

This application is a continuation of pending U.S. application Ser. No. 11/453,593 filed on Jun. 15, 2006, the disclosure of which is incorporated herein by reference.

FIELD OF THE INVENTION

The present invention relates to the field of information gathering and transmission in a client/server environment and, more particularly, to techniques for localized adaptation of client devices based on correlation of events, interpretation of dynamic context or learning of detected event patterns.

BACKGROUND OF THE INVENTION

Many new computing applications involve the generation and transmission of data from a group of sensor devices to a remote "sink" node, where such data is aggregated and analyzed. Such applications are becoming common in a variety of remote monitoring scenarios, such as healthcare (where wearable sensors record and transmit various biometric measures of an individual), vehicular telematics (where on-board sensors measure various vehicular parameters and transmit them back to a central diagnostic server) and intelligent transportation systems (where highway sensors periodically record traffic conditions).

Such data gathering systems have two important goals or concerns. First, as many of these sensor devices are resource-constrained themselves (e.g., operate on batteries), the system should minimize the communication and/or the data collection overhead, helping to reduce the energy expenditure of such devices. Second, many of these devices are not just reporting nodes, but also possess a fair degree of processing power and local intelligence. Architecturally, such data collection systems comprise a set of client sensor devices that are connected (often using a wireless communications infrastructure) to a remote sink node (or server), wherein this sink node is a part of an existing information technology infrastructure.

It would be desirable for the system to allow these sensor devices to appropriately adapt their behavior without requiring significant computational or communication complexity at the sensor or client devices, even in scenarios where the devices are occasionally disconnected from a communication infrastructure and thus not necessarily communicating with the remote server.

SUMMARY OF THE INVENTION

Principles of the present invention provide techniques for localized adaptation of client devices based on correlation or learning at a remote server.

For example, in one aspect of the invention, a method for modifying a behavior of a client device in a data collection system, wherein the client device collects data and transmits data to a server, includes the following steps. The client device transmits data to the server. The server uses at least a portion of the data received from the client device to generate information that represents a modification to a behavior of the client device. The server device transmits the generated information to the client device. The client device subsequently alters the behavior of the client device based on the information received from the server.

The data transmitted to the server may include one or more data samples. Further, the data transmitted to the server may include modified statistics of the one or more data samples. Still further, the data transmitted to the server may include compressed versions of the one or more data samples.

The method may also include the server determining at least one pattern from at least a portion of the data received from the client device. For example, in one embodiment, the process of generating information may further include the use of automatic algorithms to learn, detect and analyze patterns in the reported data and infer the likelihood of patterns of future data.

The generated information that represents a modification to a behavior of the client device may include a command to modify, activate or deactivate a rule stored a-priori at the client device. Further, the generated information may include context data that affects a rule stored a-priori at the client device. Still further, the generated information may include a generated rule.

The generated rule may include a predicate which expresses at least one temporal pattern associated with the data collected by the client device. The generated rule may include a predicate which expresses characteristics of data expected to be collected by the client device. Further, the generated rule may include an action which expresses a modification to an interface of the client device. The generated rule may include an action which expresses a generation of specific content on the client device. Still further, the generated rule may include an action which expresses a modification to a behavior or content of a specific application resident on the client device. The generated rule may include an action which expresses a transmission, suppression of transmission, or compression of one or more collected data samples. In addition, the generated rule may include an action which expresses a data transformation such as, for example, an averaging operation, an outlier elimination operation, a compression operation, a filtering operation, a discrete coefficient representation (e.g., splines).

The step of the server generating a rule may further include eliminating from a predicate of the rule any attribute that cannot be locally determined by the client device. Further, the step of the server generating a rule may include specifying at least one of removal of an existing rule, refinement of an existing rule, and specification of a new rule.

The server may also use context data to generate information that represents a modification to a behavior of the client device. The context data may include data representative of context pertaining to an attribute of a user associated with the client device. The context data may include data representative of external context of one or more other individuals or entities.

The method may further include the client monitoring device resources and adjusting behavior based thereon.

Advantageously, illustrative principles of the invention provide a method for dynamically altering some aspect of the behavior of the client transmitting device, such as its data transmission rate or the generation of local alerts, based on dynamic rules that are communicated to the client device from a separate server device. Alternately, the server device may communicate a plurality of the rules in an off-line or static fashion, and may dynamically signal the client device to activate or deactivate a set of such a-priori downloaded rules.

These dynamic rules may usually be generated based on external context data or the information previously transmitted by the device, and may typically inform the device of either the expected pattern of data samples that the sensor generates or an intermediary client gateway device receives from an individual sensor (for which no action is often needed) or the unexpected data patterns (for which specific action is desired). Furthermore, the rules may have predicates that refer to context data (including, but not limited to, the resources of the client device, the contextual attributes locally available to the client device, the data collected by the client device), and the client device may be expected to process events to recognize when such predicates are valid. Similarly, the action part of the rules may involve modification of the data collection behavior from the sensors (such as their reporting frequency, resolution, etc.), the data transmission behavior (such as the type of statistic transmitted, the amount of lossy or lossless compression employed, etc.) or the behavior of the client device (such as the setting of calendar entries, alarms, etc.)

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 5 illustrates a rule specification, according to an embodiment of the present invention.

FIG. 6 illustrates a computing system architecture with which a client and/or a server associated with a data collection system may be implemented, according to an embodiment of the present invention.

DETAILED DESCRIPTION OF PREFERRED EMBODIMENTS

Figure 1:
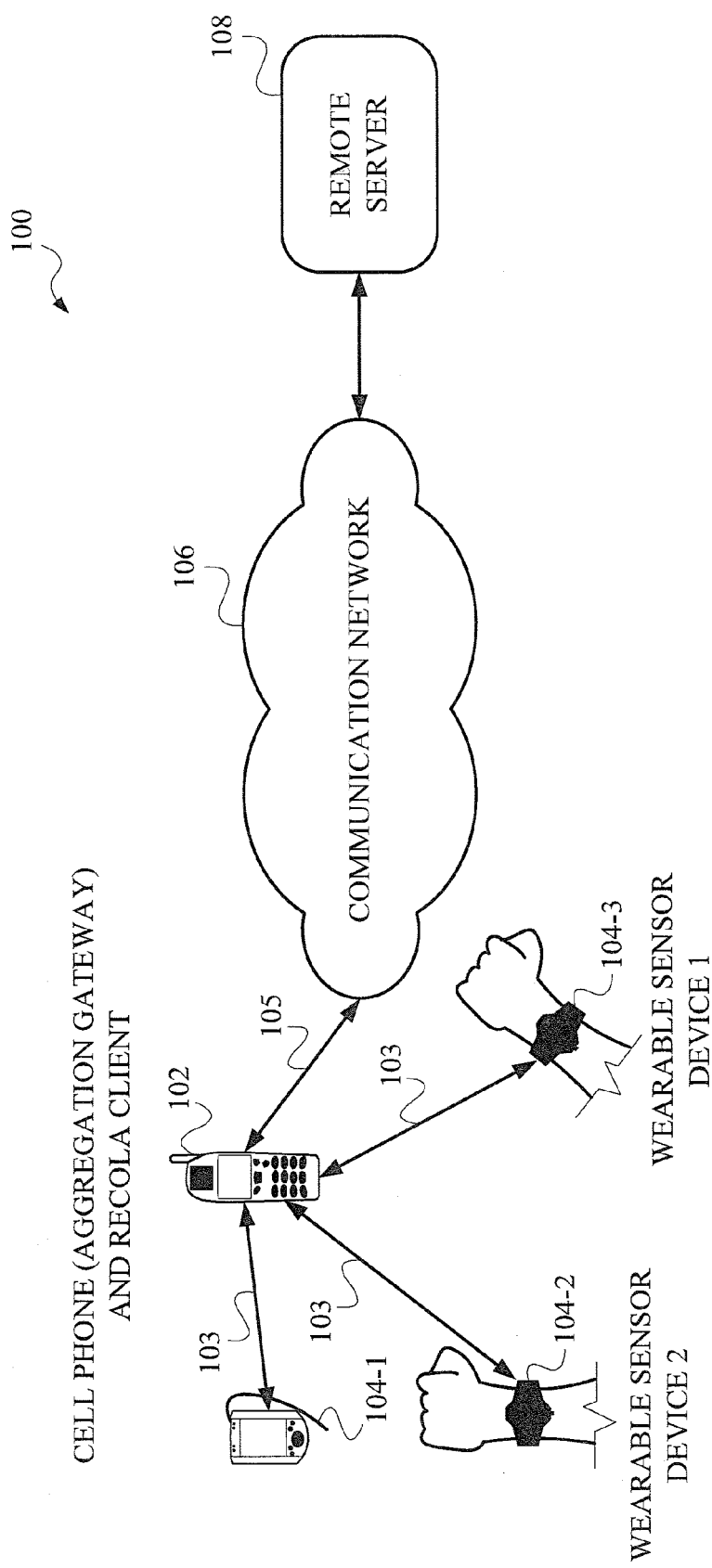
FIG. 1 illustrates a data collection system in which localized client device adaptation techniques may be implemented, according to an embodiment of the present invention.

It is to be understood that while the present invention will be described below in the context of a healthcare environment, the invention is not so limited. Rather, the invention is more generally applicable to any environment in which it would be desirable to provide localized adaptation of the behavior of a client device based on context. As used herein, the term "context" is generally understood to refer to information about the physical or virtual environment of the user and/or sensor devices and communication devices being used by the user.

It is to be appreciated that the phrase "client device" (or simply "client"), as illustratively used herein, may refer to a combination of one or more sensor devices and an intermediate gateway device acting as a client device on behalf of one or more directly connected sensor devices (as illustrated and described below in the context of FIG. 1). While the sensors and gateway may be separate devices, they may alternatively be combined into a single device. It will be evident, in the illustrative descriptions below, when the description is referring to a sensor or a gateway. However, at times, for ease of description, the sensor or the gateway, alone, may be generally referred to as a client or client device.

It is realized that it would be desirable for an information gathering and transmission (data collection) system to allow sensor devices to appropriately adapt their own behavior based on the data that they collect, even in scenarios where the devices are occasionally disconnected from a communication infrastructure and thus not necessarily communicating with the remote server.

However, it is also realized that the problems of energy-efficient adaptation and appropriate client behavior modification are intertwined. Fundamentally, energy-efficient communication techniques rely on the observation that, under ambient operating conditions, much of the data collected by a sensor network is "expected" or "predictable" (in the literature of information theory, has very low conditional entropy). Significant savings in energy and processing can be achieved if these "expected patterns of data" are known a-priori to both the client device and the server, so that information is only transmitted for the rare cases when something anomalous occurs. However, in many applications, the "expected" data pattern is time-varying, and depends not only on the contextual state of the sensor device, but on a variety of external inputs as well.

Accordingly, it is further realized that energy-efficient operation of such sensor-based applications relies on additional intelligence within the backend information technology (IT) infrastructure to determine the appropriate time-varying modifications to the behavior of the client device, and subsequently, to inform the client of these desired modifications. This additional intelligence is needed because the specific modification desired often depends on: (a) the specific characteristics of an individual application; and (b) additional, potentially dynamically changing contextual information that is unknown or unavailable to the client device or that would be too expensive in terms of communication overhead or computationally too complex for the client device to directly retrieve by interfacing with the potentially varying context sources.

Consider the example of two medical sensor devices, a heart rate monitor and a glucose monitor, that are worn by a patient being monitored. To enable remote monitoring, the devices may be programmed to sample the patient's readings once every minute, and then transmit this data over a wide-area wireless interface (e.g., such as an interface associated with General Packet Radio Service or GPRS, Universal Mobile Telecommunications System or UMTS, or IEEE 802.11) to a backend infrastructure. Alternately, these body-worn devices may use a low-range, low-power radio technology such as Bluetooth to transmit this data to a local "gateway" device, such as a cell phone. The gateway may act as a data aggregator, and may, in turn, transmit the periodically sampled data back to the server using a cellular infrastructure. Such an arrangement is illustrated in FIG. 1 and described in further detail below.

The remote server would typically monitor this data continually to detect any abnormal patterns, and when needed, may actually issue commands to the gateway (or medical devices) to trigger some behavioral modification (such as generating a voice alarm to "take your insulin shot as your glucose level is rising") based on analysis of this incoming data stream. In particular, in a sophisticated monitoring application, the remote server includes predictive components that generate such alarms (or issue other directives for modifying the behavior of client devices) not only based on current readings, but also based on estimates or predictions of the values that future samples may assume.

For example, in one embodiment of a remote healthcare monitoring application of the invention, the server may perform trend analysis to generate an early audible alarm when it detects that the glucose level is likely to rise above the acceptable level within the next 30 minutes, rather than only generate an "after-the-fact" alarm when the levels have actually crossed a critical threshold. Moreover, the actual value of this critical threshold may be patient-dependent. For example, the server may be aware that patient A is currently on a medication that potentially results in abnormally sharp rises in sugar levels, and may thus trigger an alarm for patient A at a lower threshold value than it would otherwise.

The above example illustrates both the need for periodic transmission of data from the sensor device (or the local gateway device performing aggregation) to the remote server, as well as the need for the remote server to issue or trigger appropriate behavioral modifications of the sensor device or of the client device that is acting as an intermediate aggregating of the sensor data streams. Such applications of remote monitoring are, however, often hindered by: (a) the high energy overhead in continual transmission of such data samples by the sensor device; and (b) the possibility of intermittent and, often unpredictable, network disconnection between the server and the client device (often as a result of changing wireless coverage or movement of the client device).

One technique to reduce the communication traffic back from the sensors to the sink uses the notion of a precision range or interval associated with each sensor. Such approaches essentially bound the uncertainty about the precise value of a sensor's data to a specified value. The precision range specifies an acceptable level of uncertainty, such that the sensor need not communicate its data samples back to the sink until and unless they fall outside this specified range. Precision ranges are particularly useful in many real-life applications which do not need to know the precise values of the environmental state, but can tolerate some amount of variability or inaccuracy (expressed as a tolerance measure for the application).

For example, an application monitoring glucose reading of an individual may indicate a tolerance of +/−5, implying that, after the sensor reports to the server with a value of, e.g., 130, it need not communicate back to the sink its subsequent data samples unless they exceed 135 or fall below 125. Clearly, a wider range reduces the reporting frequency of the sensor and lowers the communication overhead, since many minor variations in the sampled values, often due to noise or environmental transients, lie within the specified interval.

The U.S. patent application identified as Ser. No. 11/365,215, filed on Mar. 1, 2006, and entitled "Method for Efficient and Collective Adjustment of Sensor Reporting Ranges for Long-Lived Queries," the disclosure of which is incorporated by reference herein, discloses a technique for setting a tolerance range in applications that are concerned with aggregate statistics (such as mean, maximum or minimum) computed from a plurality of sensors. Besides demonstrating how to split the application's tolerance range into precision ranges on each individual sensor, the above-referenced U.S. patent application also discloses how such ranges could be automatically modified to account for predictable temporal variation in the data samples. However, the above-referenced U.S. patent application focuses on developing this precision range without considering the possibility that the application's tolerance range for a specific sensor's value may dynamically change due to a variety of external context.

For example, if the server became aware that patient A is currently in the gymnasium and on the treadmill (e.g., by using additional location-aware technologies such as active radio frequency identification or RFID tags), the server may determine that the person's "normal" heart rate range is now [120,135], rather than the ambient [70-85]. Moreover, precision ranges in the above-referenced U.S. patent application only focus on ways to minimize the communication overhead, but do not consider the broader issue of how other behavioral aspects of the sensor (or gateway) device may themselves change (e.g., generation of "insulin alarms") based on a combination of generated data and external context. Still further, the above-referenced U.S. patent application does not define how an intermediate relay device (the client device) may modify the data streams generated by individual sensors, by either correlating across multiple streams or through lossy/lossless compression of such streams.

The examples above illustrate the benefit that would accrue from being able to modify the communication and other behavior of a plurality of sensing devices based on a combination of context data including, but not limited to, the values of past data samples generated by the sensing devices and dynamic external context attributes relating to the device user.

One approach to our desired goal of intelligent client modification would be to deploy such context-aware computing middleware on each client device, write the application-specific logic to use such middleware and have each client device receive and process all the relevant contextual inputs. Such an approach, however, not only requires significant computing resources (powerful central processing unit or CPU, significant memory) on the client device, but also imposes high communication overhead on the client since it must now, often continuously, receive such contextual data.

For example, to intelligently alter the precision range of the heart-rate monitor when its wearer is exercising in the gymnasium, the monitor would not only have to be configured with the identity of its wearer, but must continually access the communication infrastructure to retrieve various other attributes (such as the current location of the individual) from other sources of context. Moreover, in many cases, some of the contextual data (e.g., in the healthcare scenario, the medication history for a patient) might be sensitive or subject to privacy concerns, and might be made available directly only to a trusted, centralized server, and not to individual, mobile, sensor devices or aggregation gateways. Finally, to continually receive updates on changes in the values of context data attributes, the above approaches would require the individual sensor devices to be continuously connected to the infrastructure network.

Broadly speaking, any such context-dependent behavior of any computing device may be described via rules, where each rule comprises the following constituent components: (a) a "predicate" component that specifies the precise set of contextual conditions (e.g., "the current heart rate exceeds 150," "the current location is 19 Skyline Drive") under which the rule is considered valid; and (b) an "action" component that specifies the resulting behavior of the device. Note that the above examples illustrate how the energy-efficient operation of monitoring-driven applications may require time-varying changes to: (a) the "predicate" component (for example, the modification of the tolerance range when the user is in the gymnasium); or (b) the "action" component (e.g., the instantaneous transmission of "critical" data versus the local storage of "normal" samples for retrieval at a later time or changing the compression level employed to the data stream before it is transmitted back to the backend server).

Accordingly, principles of the invention provide a system and method by which the behavior (not just restricted to their communication overhead) of a plurality of sensor devices can be dynamically modified, based on a variety of context (including, but not limited to, the past pattern of data reported by an individual sensor) without requiring: (a) continuous transmission of all data samples back to a central server; (b) continuous connectivity of the sensor device to the network infrastructure; or (c) direct retrieval by the sensor device or the intermediate client gateway device of all the contextual data needed for triggering such modification.

It is to be appreciated that modification may be based on both the spatio-temporal variation in data samples reported by the sensor nodes and additional external context. The behavioral modification allows the client sensor nodes to both reduce their communication overhead and maintain the level of responsiveness required by the application, without requiring the client devices to necessarily be continuously connected to the server over a communication network. Illustrative principles of the invention use a system architecture, referred to herein as Remote Correlation and Local Adaptation (RECOLA), which provides for energy-efficient adaptation of client (sensor) node behavior for continual monitoring applications.

In RECOLA, a remote server node (alternatively referred to as a "sink") contains the bulk of the computational logic to determine the current (or future) desired behavior of the client device, and is also aware of various other contextual data that may affect the desired behavior of the client device. The individual client devices may directly connect to the server node, or may have their data funneled through an aggregation gateway. The behavioral modification may be affected at either the sensor devices or at the aggregation gateway. The server may include an optional "learning" component that analyzes the past contextual history of the client devices and other environmental state to determine the appropriate "rules" determining the future action desired in the client devices.

The client devices or the intermediate client gateway device may not always be network-connected, and so, are unlikely to be in continuous communication with the remote server. Accordingly, the system provides a method by which the remote server is able to instruct the client device of potential changes to its expected behavior, where the behavior may relate to the processing and transmission of data samples generated by the client device, or other actions (e.g., an audible alarm, change in data sampling frequency, quantization level used in the sampling process) associated with the client device.

FIG. 1 illustrates a data collection system in which localized client device adaptation techniques may be implemented, according to an embodiment of the present invention.

As shown, system 100 includes aggregation gateway 102 (in this embodiment, a cell phone, although other types and quantities of gateways may be employed) which is in communication with a plurality of sensors 104-1 through 104-3 (note that more or less sensors can be employed) via short-range Bluetooth links 103. In accordance with the healthcare scenario, one or more of the sensors can be a health monitor which monitors some health characteristic of the user (wearer), e.g., heart rate, glucose level, etc. In the RECOLA architecture, aggregation gateway 102 is known as a RECOLA client. It is to be understood that the system can include more RECOLA clients. However, for simplicity, only one client is shown.

System 100 also includes remote server 108 (again, note that the system can include more than one remote server).

Client 102 is in communication with server 108 via a wide-area wireless link 105 and a communication network 106 (such as the Internet or World Wide Web). It is to be understood that the links shown in FIG. 1 are for illustration purposes only and, thus, alternative communications mechanisms may be employed to link a RECOLA client with a remote server.

Figure 2:
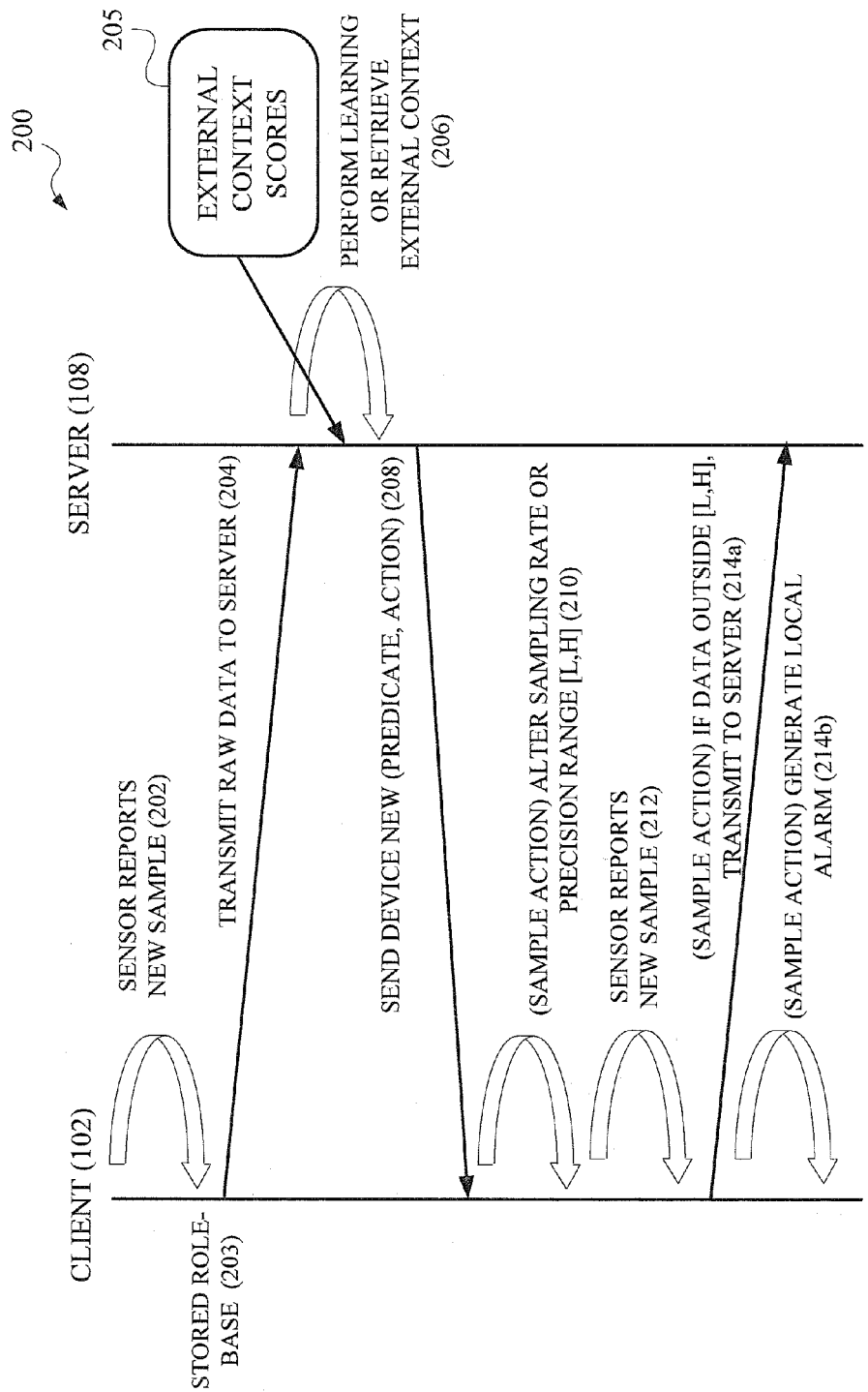
FIG. 2 illustrates a methodology for localized client device adaptation, according to an embodiment of the present invention.

FIG. 2 illustrates a methodology for localized client device adaptation, according to an embodiment of the present invention. More particularly, FIG. 2 illustrates the steps taken at and between a RECOLA client (e.g., aggregation gateway 102 of FIG. 1) and a RECOLA server (e.g., remote server 108 of FIG. 1).

As shown, in step 202, sensors (e.g., 104-1, 104-2 and/or 104-3 of FIG. 1) report new sample data. The sensor devices generate sensor data samples at appropriate intervals (202). Client 102 compares such data against a stored rule-base 203 (a database containing rules) to see if the resulting data pattern matches any predicate in the rule-base, and performs the resulting action specified in the matched rule. One action may be to transmit the data sample to server 108 (step 204). It is to be appreciated that the comparison is against "active" rules in the rule-base, wherein the rule-base may have a superset of rules downloaded a-priori.

In step 206, the server then uses such transmitted data samples, as well as additional contextual data from additional sources 205, along with application-specific logic (described further below in the context of FIG. 4), to determine any new rules or modifications to existing rules for a specific client, such that the predicates for these rules only involve contextual conditions that may be locally determined by the client. Such contextual conditions may involve additional data events reported by the sensors, the resource levels of the gateway or sensor devices (e.g., the battery level of the gateway) or some local context (e.g., for a GPS-enabled phone, the current location of the phone).

In step 208, the server communicates such updated rules to the client device, which then stores these rules in its rule-base, so that the client behavior at future time instants or for subsequently generated data samples is appropriately modified. Alternatively, rather than the server communicating the updated rule to the client, one of the following steps may occur. In one alternative embodiment, the server may update an identifier (ID) of activated/deactivated rules or the changed parameters/threshold of such rules. In a second alternative embodiment, the server may push the necessary "context" conditions that are required by the predicates of active rules on the client, and thus require the client to then locally determine which of its rules are triggered or invalidated by these new "context" conditions. Thus, in general, the server sends information representative of appropriate knowledge of modification of currently applicable rules to the client. It is to be appreciated that such information (whether complete or partial rules, IDs, and/or context data) may be sent dynamically or a-priori to the client device.

By way of example, as illustrated in step 210, an action that the new rule may specify is for the client (i.e., one of its sensors) to alter its sampling rate or precision range [Low, High].

Under the new sampling rate or precision range, in step 212, the client receives a new sample from a sensor. Based on the sample, if the sample is outside the precision range, then the data is transmitted to the server (step 214a). Alternatively, or in addition to, a local alarm may be generated at the client (step 214b).

Accordingly, the methodology advantageously provides for the remote server (which does not suffer from the same resource constraints as the potentially-wearable or mobile client devices) to perform the bulk of the application-specific logic over a larger subset of context sources, and generate a rule whose predicate solely comprises contextual attributes that may be locally available to the client. For example, assume that the healthcare monitoring application's logic has the following rules:

| Predicate | Action |
| --- | --- |
| 1. if patient on medication M1, and is exercising | tolerance(heart rate) = [120,135], generate audible alarm if the average glucose readings (over 5 minute window) >150. |
| 2. if patient is on medication M2 and has not taken medication M2 in the last 4 hours | |

In this case, the remote server would first determine if rule 1, was currently applicable to a patient (i.e., if the medical database listed M1 as part of the patient's medications, and if the location context indicated that the patient was in the gymnasium), and if so, would simply transmit the rule "tolerance(heart rate)=[120, 135]" to the cell phone acting as the aggregator. Similarly, if rule 2 applied, the server would instruct the client device to "generate audible alarm if the average of the last 5 glucose readings (assumed to be sampled every minute) exceeded 150 and if M2 has not been taken within the past 4 hours."

In both of these cases, the server has removed parts of the predicate (whether the person is on medication M1, or is currently in the gymnasium, and so on) that cannot be locally determined by the client from the transmitted rule, thereby enabling the client to make decisions locally. By empowering such local decision making, the RECOLA system permits local devices to exhibit responsiveness, even when they are disconnected from the network. For example, the audible alarm would be generated, even when the cell phone (the aggregation gateway) did not actually have network coverage at the time when the readings fell outside the prescribed bound.

In addition, illustrative principles of the invention are able to exploit and learn from the spatio-temporal correlation among the successive data samples collected by individual sensors. For example, the server could have one or more learning engines that would be able to analyze the raw data and determine hitherto unknown patterns in the reported data. Such unknown patterns may themselves be translated into modified precision ranges or other types of rules that are communicated back to the client device.

Such learning allows the rules to be customized for each individual, based on the specific patterns exhibited. For example, if individual A is observed to have a normal heart rate of 80, while individual B may be observed to have a long-term average heart rate of 70. This observations may be used in appropriate rules that are downloaded to the client device (e.g., user A's cell phone would have a rule to "transmit heart rate data immediately to the backend server, possibly for anomaly analysis, if the short-term average exceeds 85" whereas a similar rule for user B might set the threshold to 74).

The actual specification of the action component of the rule would depend on the specific capabilities of the computing device, and may include not just simple communication directives (e.g., transmit now, or discard data) or "alarm generations" (e.g., alert user via beeps), but also more sophisticated processing and storage of the data samples. For example, in certain applications where the data comprises continuous waveforms, it may be acceptable to actually capture the waveform's properties through varying numbers of discrete coefficients (e.g., splines) or apply different levels of lossy compression, depending on the actual data values.

Furthermore, to address periods when the client device is disconnected from the communications infrastructure, context-specific rules (such as the increased heart rate thresholds which apply during workouts in a gymnasium) can be made to be transient, or have its active duration be a direct function of locally available context (e.g., on a GPS enabled phone, a rule could be triggered to be applicable only when location is within a specified zone). Such rules would apply for a period of time and then timeout, allowing the client device to return to "normal" states of monitoring.

Figure 3:
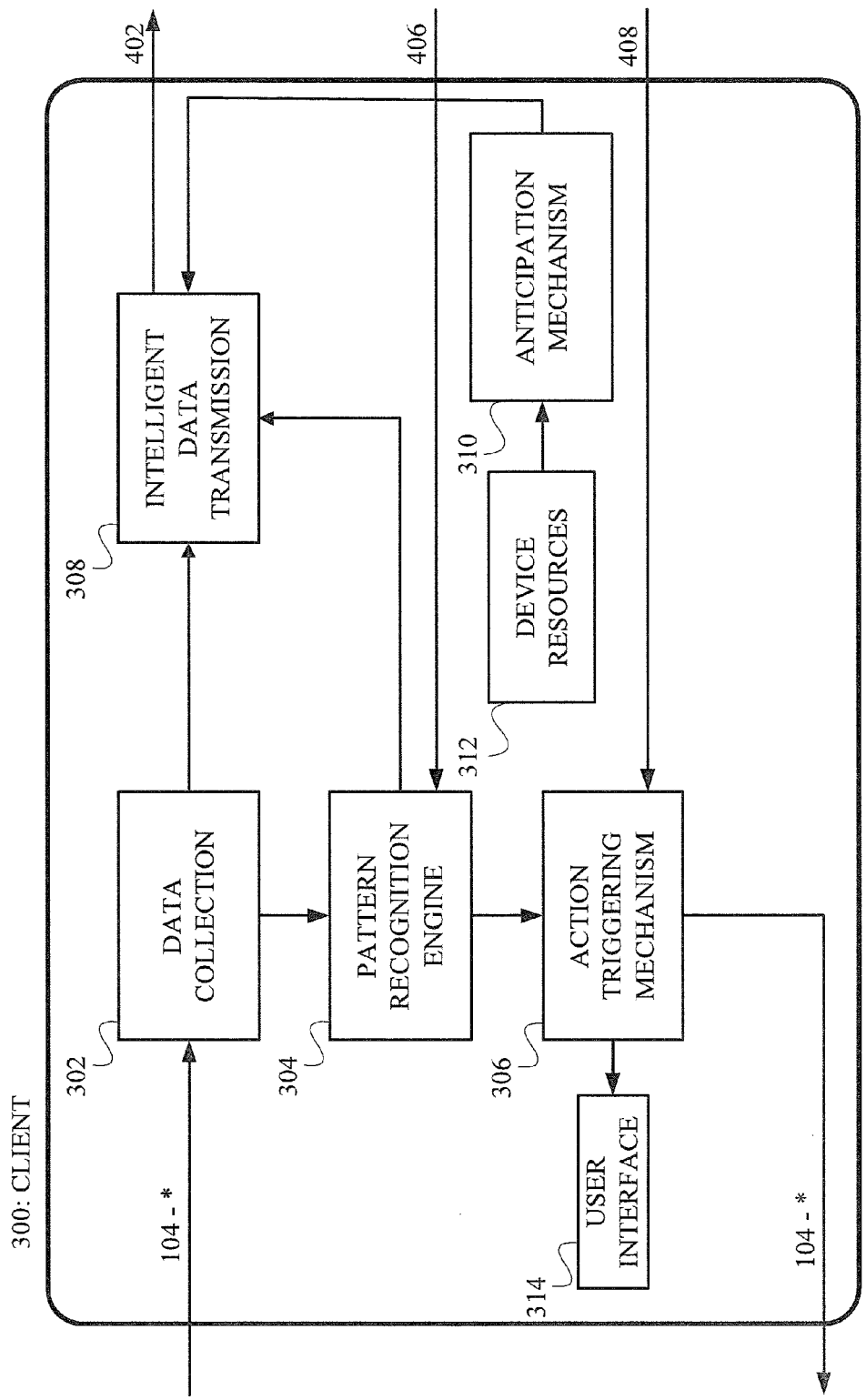
FIG. 3 illustrates a client in which localized client device adaptation techniques may be implemented, according to an embodiment of the present invention.

FIG. 3 illustrates a client in which localized client device adaptation techniques may be implemented, according to an embodiment of the present invention.

As shown, client 300 comprises data collection component 302, pattern recognition engine 304, action triggering mechanism 306, intelligent data transmission component 308, anticipation mechanism 310, device resources component 312, and user interface component 314.

Data collection component 302 collects raw sensor data from sensors 104-1 through 104-3 (e.g., heart monitor, glucose monitor). The sensor data is provided to pattern recognition engine 304. Pattern recognition engine 304 detects when known patterns occur in the incoming sensor stream. When a known pattern is detected, engine 304 alerts action triggering mechanism 306.

Action trigger mechanism 306 relays user notifications via the client's user interface 314 (e.g., display, speaker, audible alerts, tactile alerts). Mechanism 306 can also control the sensors 104-1 through 104-3 (e.g., turn them on or off, change their frequency of collection, etc.). Mechanism 306 may trigger other actions.

Data collection component 302 also passes raw sensor data to intelligent data transmission component 308 whose function is to determine whether to send this data to data processing unit 402 on server 400 (to be described below in the context of FIG. 4). To make this determination, information is also collected from pattern recognition engine 304 (e.g., information indicating whether this data stream is normal or abnormal) and from anticipation mechanism 310.

Anticipation mechanism 310 monitors device resources 312 in light of historical trends. As the device resources are depleted or expected to run low, the threshold for data transmission increases and intelligent data transmission component 308 throttles the amount of data transmitted to data processing component 402 on server 400.

It should be noted that pattern recognition engine 304 receives pattern specifications from pattern learning engine 406 of server 400 (to be described below in the context of FIG. 4). In an alternative embodiment, client 300 could also contain a pattern learning engine that could either replace the server-side component or could augment it.

It should also be noted that action triggering mechanism 306 can also receive action triggers from pattern recognition engine 408 on server 400.

Note also that, in one embodiment, the client may monitor device resources and adjust behavior appropriately. For example, if power is a concern, then the device can store data locally or perform additional compression on the data to avoid the power-intensive transmission of extra data.

It is to be appreciated that block 300 may be considered as a combination of aggregation gateway 102 and sensor devices 104-1 through 104-3. That is, the components, while shown separately in FIG. 1, may be combined in one client device.

Figure 4:
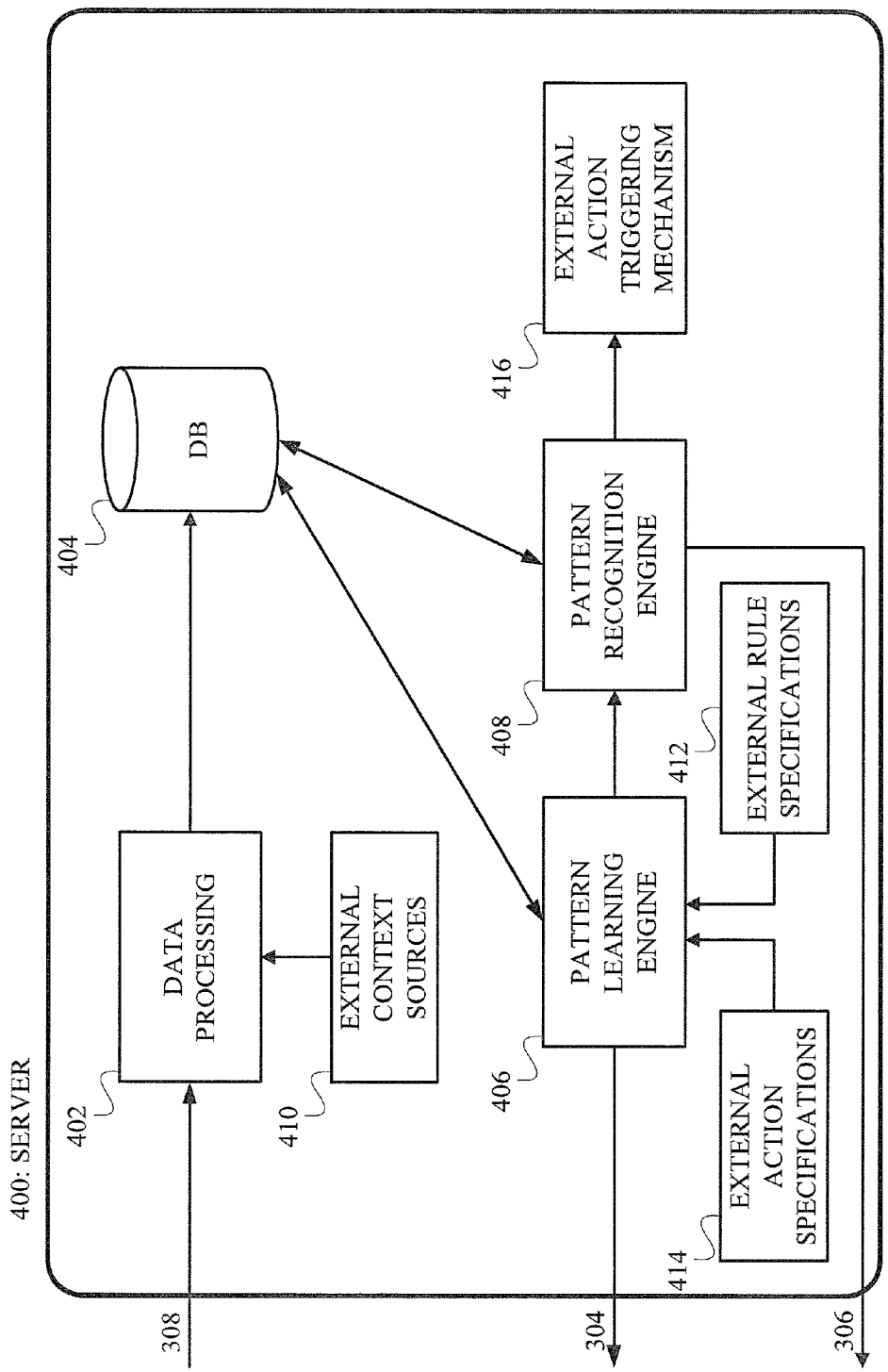
FIG. 4 illustrates a server in which localized client device adaptation techniques may be implemented, according to an embodiment of the present invention.

FIG. 4 illustrates a server in which localized client device adaptation techniques may be implemented, according to an embodiment of the present invention. It should be appreciated that alternate designs are also possible.

As shown, server 400 comprises data processing module 402, database 404, pattern learning engine 406, pattern recognition engine 408, external context sources 410, external rule specifications 412, external action specifications 414, and external action triggering mechanism 416. It is to be appreciated that block 400 may be considered as a combination of remote server 108 and external context sources 205. That is, the components, while shown separately in FIG. 2, may be combined in one server device.

Data processing module 402 receives data transmitted by intelligent data transmission component 308 of client 300 (FIG. 3). Module 402 sends this data to database 404. Similarly, data processing module 402 also receives external context data 410. Module 402 also sends this data to database 404.

Pattern learning engine 406 retrieves data from database 404. Pattern learning engine 406 may operate in an online fashion (as and when new data samples arrived) or may be triggered periodically at appropriately determined time intervals. Engine 406 identifies patterns in this data and creates rules to specify those patterns. These rule specifications are relayed to pattern recognition engine 304 on client 300. They are also relayed to pattern recognition engine 408 on server 400. Once a pattern is recognized, an action can be associated with that pattern via external action specification component 414. It is to be appreciated, as described above, that the rules generated for the client may advantageously only involve contextual conditions that are locally determined by the client and consequently may differ from those maintained on the server.

It is to be appreciated that pattern learning engine 406 and pattern recognition engine 408 may subscribe to database updates from database 404 rather than retrieving data explicitly.

It is also to be appreciated that rule specifications can be received by the pattern learning engine 406 from external source 412. These externally specified rules can then be passed to both pattern recognition engine 304 of the client and pattern recognition engine 408 of the server. For example, a physician could specify a medically significant event that merits action, but has not been observed in a particular patient.

Pattern recognition engine 408 uses the rule specifications to identify patterns in the received sensor data previously stored in database 404. Upon identifying a pattern, engine 408 can trigger actions through action triggering mechanism 306 on the client. Likewise, engine 408 can trigger external actions (e.g., notification to physician) through external action triggering mechanism 416.

FIG. 5 illustrates a rule specification 500, which contains a unique rule identifier 502, a pattern specification 504 and an action specification 506. The pattern specification 504 can be defined in many ways, such as regular expressions or Extensible Markup Language (XML). The action specification 506 can also be defined in many ways. It can be an identifier from a repository of actions (e.g., notifications, audible alarms, visible displays, etc). It could also be a specification of a program executable via a language such as XML.

FIG. 6 illustrates a computer system in accordance with which one or more components/steps of a data collection system (e.g., components/steps described in the context of FIGS. 1 and 5) may be implemented, according to an embodiment of the present invention. That is, the architecture shown in FIG. 6 may represent an architecture used to implement all or some of the components of aggregation gateway 102, each of sensors 104-1 through 104-3, and/or remote server 108.

Further, it is to be understood that the individual components/steps may be implemented on one such computer system, or more preferably, on more than one such computer system. In the case of an implementation on a distributed system, the individual computer systems and/or devices may be connected via a suitable network (e.g., the Internet or World Wide Web). However, the system may be realized via private or local networks. The invention is not limited to any particular network.

As shown, the computer system 600 may be implemented in accordance with a processor 602, a memory 604, I/O devices 606, and a network interface 608, coupled via a computer bus 610 or alternate connection arrangement.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc.

In addition, the phrase "input/output devices" or "I/O devices" as used herein is intended to include, for example, one or more input devices (e.g., keyboard, mouse, etc.) for entering data to the processing unit, and/or one or more output devices (e.g., speaker, display, etc.) for presenting results associated with the processing unit.

Still further, the phrase "network interface" as used herein is intended to include, for example, one or more transceivers to permit the computer system to communicate with another computer system via an appropriate communications protocol.

Accordingly, software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

It is to be further appreciated that the present invention also includes techniques for providing user data collection services. By way of example, a service provider agrees (e.g., via a service level agreement or some informal agreement or arrangement) with a service customer to provide user data collection services. That is, by way of one example only, the service provider may host the customer's web site and associated applications (e.g., healthcare monitoring, etc.). Then, in accordance with terms of the contract between the service provider and the service customer, the service provider provides user data collection services which may include one or more of the methodologies of the invention described herein. By way of example, this may include collecting sample data from a client (of the service customer) and localized adaptation of the client device so as to provide one or more benefits to the service customer. The service provider may also provide one or more of the context sources used in the process. For example, the service provider may provide location context, or electronic calendar services.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for modifying a behavior of a client device in a data collection system wherein the client device collects data and transmits data to a server, the method comprising the steps of:
the client device transmitting data to the server; the server using at least a portion of the data received from the client device to generate information that is used to modify a target behavior of the client device, wherein said generated information comprises contextual information that is not locally available to the client device and which is relevant to modifying the target behavior of the client device, wherein the contextual information comprises context data about a user of the client device, wherein the context data comprises information about a condition of the user or the user's environment, which dynamically varies and is unknown or unavailable to the client device;
the server device transmitting the generated information with said contextual information to the client device; and
the client device subsequently modifying the target behavior of the client device based on the generated information received from the server at times when the client device is connected to the server and based on the generated information that was previously received from the server at times when the client device is disconnected from the server,
wherein the client device modifies the target behavior by using the contextual information received from the server to determine one or more locally stored rules on the client, which are triggered, modified or invalidated based on the contextual information,
wherein each of the one or more locally stored rules include a predicate component that specifies a contextual condition under which the rule is considered valid, and an action component that specifies a resulting behavior of the client device,
wherein the contextual information is used by the client device to determine which of a plurality of locally available predicate or action components of the locally stored rules is applicable at a given time, and select a predicate or action component of a given one of the locally stored rules that is determined to be applicable at the given time.

2. The method of claim 1, wherein the data transmitted to the server comprises one or more data samples.

3. The method of claim 2, wherein the data transmitted to the server comprises modified statistics of the one or more data samples.

4. The method of claim 2, wherein the data transmitted to the server comprises compressed versions of the one or more data samples.

5. The method of claim 1, further comprising the step of the server determining at least one pattern from at least a portion of the data received from the client device.

6. The method of claim 1, wherein the generated information comprises a command to modify, activate or deactivate a rule stored a-priori at the client device.

7. The method of claim 1, wherein the generated information comprises a generated rule.

8. The method of claim 7, wherein the generated rule comprises a predicate which expresses at least one temporal pattern associated with the data collected by the client device.

9. The method of claim 7, wherein the generated rule comprises a predicate which expresses characteristics of data expected to be collected by the client device.

10. The method of claim 7, wherein the generated rule comprises action which expresses a modification to an interface of the client device.

11. The method of claim 7, wherein the generated rule comprises an action which expresses a generation of specific content on the client device.

12. The method of claim 7, wherein the generated rule comprises an action which expresses a modification to a behavior or content of a specific application resident on the client device.

13. The method of claim 7, wherein the generated rule comprises an action which expresses a transmission, suppression of transmission, or compression of one or more collected data samples.

14. The method of claim 7, wherein the generated rule comprises an action which expresses a data transformation.

15. The method of claim 14, wherein the data transformation comprises at least one of an averaging operation, an outlier elimination operation, a compression operation, a filtering operation, a discrete coefficient representation.

16. The method of claim 7, wherein the step of the server generating a rule further comprises eliminating from a predicate of the rule any attribute that cannot be locally determined by the client device.

17. The method of claim 7, wherein the step of the server generating a rule further comprises specifying at least one of removal of an existing rule, refinement of an existing rule, and specification of a new rule.

18. The method of claim 1, wherein the server also uses context data to generate information that represents a modification to a behavior of the client device.

19. The method of claim 18, wherein the context data comprises data representative of context pertaining to an attribute of a user associated with the client device.

20. The method of claim 18, wherein the context data comprises data representative of external context of one or more other individuals or entities.

21. The method of claim 1, further comprising the client monitoring device resources and adjusting behavior based thereon.

22. A method, for use in a client device, for modifying a behavior of the client device in a data collection system wherein the client device collects data and transmits data to a server, the method comprising the steps of:
transmitting data to the server such that the server is able to use at least a portion of the data received from the client device to generate information that is used to modify a target behavior of the client device, wherein said generated information comprises contextual information that is not locally available to the client device and which is relevant to modifying the target behavior of the client device, wherein the contextual information comprises context data about a user of the client device, wherein the context data comprises information about a condition of the user or the user's environment, which dynamically varies and is unknown or unavailable to the client device; and
subsequently modifying the target behavior of the client device based on the generated information received from the server at times when the client device is connected to the server and based on the generated information that was previously received from the server at times when the client device is disconnected from the server, wherein the client device modifies the target behavior by using the contextual information received from the server to determine one or more locally stored rules on the client, which are triggered, modified or invalidated based on the contextual information, wherein each of the one or more locally stored rules include a predicate component that specifies a contextual condition under which the rule is considered valid, and an action component that specifies a resulting behavior of the client device, wherein the contextual information is used by the client device to determine which of a plurality of locally available predicate or action components of the locally stored rules is applicable at a given time, and select a predicate or action component of a given one of the locally stored rules that is determined to be applicable at the given time.

23. The method of claim 22, wherein the generated information comprises a command to modify, activate or deactivate a rule stored a-priori at the client device.

24. The method of claim 22, wherein the generated information comprises context data that affects a rule stored a-priori at the client device.

25. The method of claim 22, wherein the generated information comprises a generated rule.

26. The method of claim 22, further comprising the client monitoring device resources and adjusting behavior based thereon.

27. A method, for use in a server, for modifying a behavior of a client device in a data collection system wherein the client device collects data and transmits
data to the server, the method comprising the steps of: receiving data from the client device; using at least a portion of the data received from the client device to generate information that is used to modify a target behavior of the client device, wherein said generated information comprises contextual information that is not locally available to the client device and which is relevant to modifying the target behavior of the client device, wherein the contextual information comprises context data about a user of the client device, wherein the context data comprises information about a condition of the user or the user's environment, which dynamically varies and is unknown or unavailable to the client device; and transmitting the information with said contextual information to the client device such that the client device is able to subsequently modify the target behavior of the client device based on the generated information received from the server at times when the client device is connected to the server and based on the generated information that was previously received from the server at times when the client device is disconnected from the server, wherein the contextual information is usable by the client device to locally determine one or more locally stored rules on the client, which are triggered, modified or invalidated based on the contextual information, wherein each of the one or more locally stored rules include a predicate component that specifies a contextual condition under which the rule is considered valid, and an action component that specifies a resulting behavior of the client device, wherein the contextual information is used by the client device to determine which of a plurality of locally available predicate or action components of the locally stored rules is applicable at a given time, and select a predicate or action component of a given one of the locally stored rules that is determined to be applicable at the given time.

28. The method of claim 27, wherein the generated information comprises a command to modify, activate or deactivate a rule stored a-priori at the client device.

29. The method of claim 27, wherein the generated information comprises context data that affects a rule stored a-priori at the client device.

30. The method of claim 27, wherein the generated information comprises a generated rule.

31. The method of claim 27, wherein the client monitors device resources and adjusts behavior based thereon.

32. The method of claim 27, wherein the server also uses context data to generate information that represents a modification to a behavior of the client device.

33. Apparatus for use in a data collection system, comprising: a client device configured to:
(i) transmit data to a server such that the server is able to use at least a portion of the data received from the client device to generate information that is used to modify a target behavior of the client device, wherein said generated information comprises contextual information that is not locally available to the client device and which is relevant to modifying the target behavior of the client device, wherein the contextual information comprises context data about a user of the client device, wherein the context data comprises information about a condition of the user or the user's environment, which dynamically varies and is unknown or unavailable to the client device; and
(ii) subsequently modify the target behavior of the client device based on the generated information received from the server at times when the client device is connected to the server and based on the generated information that was previously received from the server at times when the client device is disconnected from the server, wherein the client device modifies the target behavior by using the contextual information received from the server to locally determine one or more locally stored rules on the client, which are triggered, modified or invalidated based on the contextual information, wherein each of the one or more locally stored rules include a predicate component that specifies a contextual condition under which the rule is considered valid, and an action component that specifies a resulting behavior of the client device, wherein the contextual information is used by the client device to determine which of a plurality of locally available predicate or action components of the locally stored rules is applicable at a given time, and select a predicate or action component of a given one of the locally stored rules that is determined to be applicable at the given time.

34. Apparatus for use in a data collection system, comprising: a server configured to:
(i) receive data from a client device;
(ii) use at least a portion of the data received from the client device to generate information that is used to modify a target behavior of the client device, wherein said generated information comprises contextual information that is not locally available to the client device and which is relevant to modifying the target behavior of the client device;

wherein the contextual information comprises context data about a user of the client device, wherein the context data comprises information about a condition of the user or the user's environment, which dynamically varies and is unknown or unavailable to the client device; and (iii) transmit the generated information with said contextual information to the client device such that the client device is able to subsequently modify the target behavior of the client device based on the generated information received from the server at times when the client device is connected to the server and based on the generated information that was previously received from the server at times when the client device is disconnected from the server, wherein the contextual information is usable by the client device to determine one or more locally stored rules on the client, which are triggered, modified or invalidated based on the contextual information, wherein each of the one or more locally stored rules include a predicate component that specifies a contextual condition under which the rule is considered valid, and an action component that specifies a resulting behavior of the client device, wherein the contextual information is used by the client device to determine which of a plurality of locally available predicate or action components of the locally stored rules is applicable at a given time, and select a predicate or action component of a given one of the locally stored rules that is determined to be applicable at the given time.

* * * * *